US006948252B2

(12) United States Patent
Gibson (10) Patent No.: US 6,948,252 B2
(45) Date of Patent: Sep. 27, 2005

(54) LIGHT PROJECTING GONIOMETER

(76) Inventor: William F. Gibson, HC 68 Box 7, Renick, WV (US) 24966

( * ) Notice: Subject to any disclaimer, the term of this patent is extended or adjusted under 35 U.S.C. 154(b) by 36 days.

(21) Appl. No.: 10/375,419

(22) Filed: Feb. 27, 2003

(65) Prior Publication Data

US 2003/0226268 A1 Dec. 11, 2003

Related U.S. Application Data

(60) Provisional application No. 60/360,122, filed on Feb. 28, 2002.

(51) Int. Cl.$^7$ .................................................. G01B 3/56
(52) U.S. Cl. ........................... 33/1 PT; 33/276; 33/278; 33/286
(58) Field of Search ................................ 33/1 PT, 1 N, 33/286, 281–282, 285, 275 R, DIG. 21, 76–279

(56) References Cited

U.S. PATENT DOCUMENTS

| 3,614,414 | A | * | 10/1971 | Gores ......................... 362/573 |
| 3,634,838 | A | | 1/1972 | Grandvist |
| 3,897,637 | A | * | 8/1975 | Genho ......................... 33/227 |
| 4,125,864 | A | | 11/1978 | Aughton |
| 4,442,606 | A | * | 4/1984 | Graham et al. .............. 33/1 N |
| 4,645,302 | A | | 2/1987 | Aughton |
| 4,665,928 | A | | 5/1987 | Linial et al. |
| 4,883,069 | A | | 11/1989 | McLeod |
| 4,908,948 | A | * | 3/1990 | Gormley ....................... 33/276 |
| 5,189,799 | A | | 3/1993 | Fairer et al. |
| 5,263,492 | A | | 11/1993 | Voyce |
| 5,539,990 | A | * | 7/1996 | Le ................................ 33/283 |
| 5,713,135 | A | * | 2/1998 | Acopulos ..................... 33/451 |
| 5,788,359 | A | * | 8/1998 | Halsey et al. ............... 362/118 |
| 5,822,124 | A | | 10/1998 | Matsuda et al. |
| 5,832,422 | A | | 11/1998 | Wiedenhoefer |
| 5,836,081 | A | * | 11/1998 | Orosz, Jr. ..................... 33/290 |
| 5,864,956 | A | * | 2/1999 | Dong ........................... 33/227 |
| 5,983,510 | A | * | 11/1999 | Wu et al. ..................... 33/227 |
| 6,195,902 | B1 | * | 3/2001 | Jan et al. ..................... 33/286 |
| 6,428,490 | B1 | | 8/2002 | Kramer et al. |
| 6,453,568 | B1 | * | 9/2002 | Hymer ......................... 33/276 |
| 6,497,051 | B1 | * | 12/2002 | Poole et al. ................. 33/784 |
| 6,560,560 | B1 | * | 5/2003 | Tachner ....................... 702/164 |
| 6,718,643 | B2 | * | 4/2004 | Tamamura ................... 33/286 |
| 2001/0037581 | A1 | * | 11/2001 | Akhavan-Sigari et al. .... 33/807 |
| 2002/0152621 | A1 | * | 10/2002 | Letourneau .................. 33/277 |

FOREIGN PATENT DOCUMENTS

FR 617258 A1 * 9/1994

OTHER PUBLICATIONS

Bronzino, Joseph, ed.,The Biomedical Engineering Handbook, CRC Press LLC, 1995; p. 2177–2182.
McGraw Hill Encyclopedia of Science & Technology; vol. a–azu; p. 427.

* cited by examiner

Primary Examiner—G. Bradley Bennett
Assistant Examiner—Tania C. Courson
(74) Attorney, Agent, or Firm—Basch & Nickerson LLP; Duane C. Basch (57) ABSTRACT

This device is a handheld, battery-operated instrument that utilizes light beams to project visible lines for increasing the accuracy in determining angles. A linear potentiometer is incorporated at the pivot point between the two diodes and measures a voltage change based on the angle between the arms of the device.

5 Claims, 6 Drawing Sheets

LIGHT PROJECTING GONIOMETER

CROSS-REFERENCE TO RELATED PATENT APPLICATIONS

This patent application claims priority based on provisional application U.S. Ser. No. 60/360,122, filed on Feb. 28, 2002.

FIELD OF THE INVENTION

An apparatus for measuring the angle between two rays, wherein the apparatus comprises a light source for generating a first light beam and a second light beam, a means for aligning these light beams to determine an angle to be measured.

BACKGROUND OF THE INVENTION

A goniometer is a device for measuring or setting angles. Prior art goniometers have utilized a number of principles to determine angles. Reference may be had, for example, to The Biomedical Engineering Handbook (Joseph D. Bronzino Ed., CRC Press LLC, 1995) pages 2177–2182.

Prior art goniometer designs include the following categories; Universal, Arthroidial, Fluid, Pendulum, Myrin OB, and Electrogoniometer.

The Universal Goniometer comprises a protractor-like measuring device with one movable arm and one stationary arm. The two arms are superimposed on the rays of the angle, and the measurement may be read on the protractor. Often, several goniometers of different sizes are required to measure different digits (i.e. a knee versus a finger). Additionally, the increments on the protractor limit the sensitivity of the measurement to the gradations on the instrument. The placement of the arms is also a source of error, as it is difficult to properly align relatively small arms parallel to a large extremity. Providing longer arms on the device may compensate, but this negatively impacts the portability of the device. Reference may be had, for example, to The Biomedical Engineering Handbook (Joseph D. Bronzino Ed., CRC Press LLC, 1995) page 2181.

The Arthroidial goniometer is a single protractor, similar to the Universal goniometer, but lacking arms. These instruments likewise suffer the same drawbacks. Reference may be had, for example, to The Biomedical Engineering Handbook (Joseph D. Bronzino Ed., CRC Press LLC, 1995) page 2181.

Fluid and Pendulum Goniometers utilize gravity to aid in measuring angles. Fluid goniometers contain a fluid-filled channel with an air bubble that moves as the device changes its angle relative to the gravitational plane. Likewise, Pendulum goniometers contain a pendulum for detecting angular changes. Such goniometers are often more accurate than their universal counterparts, but are additionally more expensive. Reference may be had, for example, to The Biomedical Engineering Handbook (Joseph D. Bronzino Ed., CRC Press LLC, 1995) page 2181.

Myrin Goniometers exploit a combination of gravity sensing devices and magnetic field sensing devices that respond to the Earth's magnetic field. These goniometers are often bulky and useless for measuring the angles associated with small joints, such as the fingers. They additionally suffer to electromagnetic interference. Reference may be had, for example, to The Biomedical Engineering Handbook (Joseph D. Bronzino Ed., CRC Press LLC, 1995) page 2181.

Electrogoniometers are physically strapped to the proximal and distal portions of the joint to be measured. These devices are inherently cumbersome and expensive. Each electrogoniometer is designed for specific body parts and they are typically used only as pieces of laboratory equipment. Reference may be had, for example, to The Biomedical Engineering Handbook (Joseph D. Bronzino Ed., CRC Press LLC, 1995) page 2181.

By way of further illustration, U.S. Pat. No. 3,634,838 discloses a goniometer arrangement that allows for the digital display of the measured angle. Such a digital display circumvents the difficulties associated with protractor measurements, such as being limited to the increments marked on the protractor.

U.S. Pat. No. 4,665,928 of Linial teaches the use of pendulum goniometers to determine angles on a living person. This patent also discloses the use of potentiometers to digitize the measurement, thus avoid protractor-like measurements.

U.S. Pat. No. 4,883,069 discloses an electrogoniometer that physically attaches to a joint through the use of straps.

U.S. Pat. No. 5,189,799 discloses a goniometer comprised of a single laser to determine the angle of a geographic feature.

U.S. Pat. No. 5,832,422 discloses a hand-held measuring device that is capable of measuring angles. The device tracks the angle the device is moved as it proceeds from a first position to a second position.

U.S. Pat. No. 6,428,490 discloses a series of resistive bend sensors that may be built into a garment to measure the range of motion for computer animation, for example. Such a suit would be undesirable for simple medical measurements due to the size of the device, its complexity, and its cost.

In spite of the substantial amount of prior art disclosing goniometers, these prior art goniometers suffer from a number of disadvantages. Many of the prior art instruments utilize manual, as opposed to digital, measurements, which inherently limit the precision of the measurements to the gradations on the protractor. Additionally, many prior art angle-measuring devices must use long arms in order to accurately visualize the rays of the angle to be measured. These long arms make these devices cumbersome and unsuitable for use with small joints. Additionally, many of the prior art goniometers are expensive, and difficult to transport, diminishing their usefulness as everyday instruments.

The instant invention seeks to overcome all of these disadvantages and provide a measuring device that utilizes light beams in place of traditional goniometer arms. The longer the arms of a traditional goniometer, the easier it becomes to estimate the position of the ray of the angle to be measured. However, longer arms make the device less portable. The instant invention replaces the physical arms of prior art goniometers with a beam of light. The long light beams mimic the advantageous function of long arms without requiring a large volume of space. Specifically, one light beam may be aligned along the length of one section of an extremity (i.e. lower leg), while the second light beam may be aligned along the length of a second section of the same extremity (i.e. upper leg). The goniometer may read the angle between the two beams throughout the flexion and extension of the extremity. In this manner, a range of motion may be determined.

It is an object of this invention to provide a lightweight, portable, hand-held goniometer.

It is another object of this invention to provide a goniometer that can easily, and accurately estimate the position of the two rays of an angle.

It is yet another object of this invention to provide a goniometer that digitally displays an angle measurement with a high degree of precision.

It is another object of this invention to provide a goniometer that is useful on both large joints and small joints.

SUMMARY OF THE INVENTION

In accordance with this invention, there is provided an apparatus for measuring the angle formed between a first beam of light and a second beam of light, wherein said apparatus is comprised of a first light source, a second light source movably connected to said first light source, and means for determining the angle formed between said first beam of light and said second beam of light.

BRIEF DESCRIPTION OF THE DRAWINGS

The invention will be described by reference to the specification, and the drawings, in which like numerals refer to like elements, and in which.

DEFINITION OF TERMS

As used in this specification, the following terms have the meanings described hereinbelow.

The term "angle" refers to the geometric shape or arc that is defined by the intersection of two geometric rays. The term "vertex" refers to the point of intersection.

The term "ray" refers to one of the two imaginary geometric rays in an angle, extending outward from that angle's vertex. In a Universal goniometer, the two rays of an angle are visually approximated by the two arms of the goniometer. In the instant invention, one or more of the rays of an angle are visually approximated with the aid of a light beam.

Reference for these definitions may be had to, for example, The McGraw-Hill Encyclopedia of Science & Technology (Daniel N. Lapedes, Ed. McGraw-Hill, 1977) volume 1, page 427.

DESCRIPTION OF THE PREFERRED EMBODIMENTS

Figure 1:
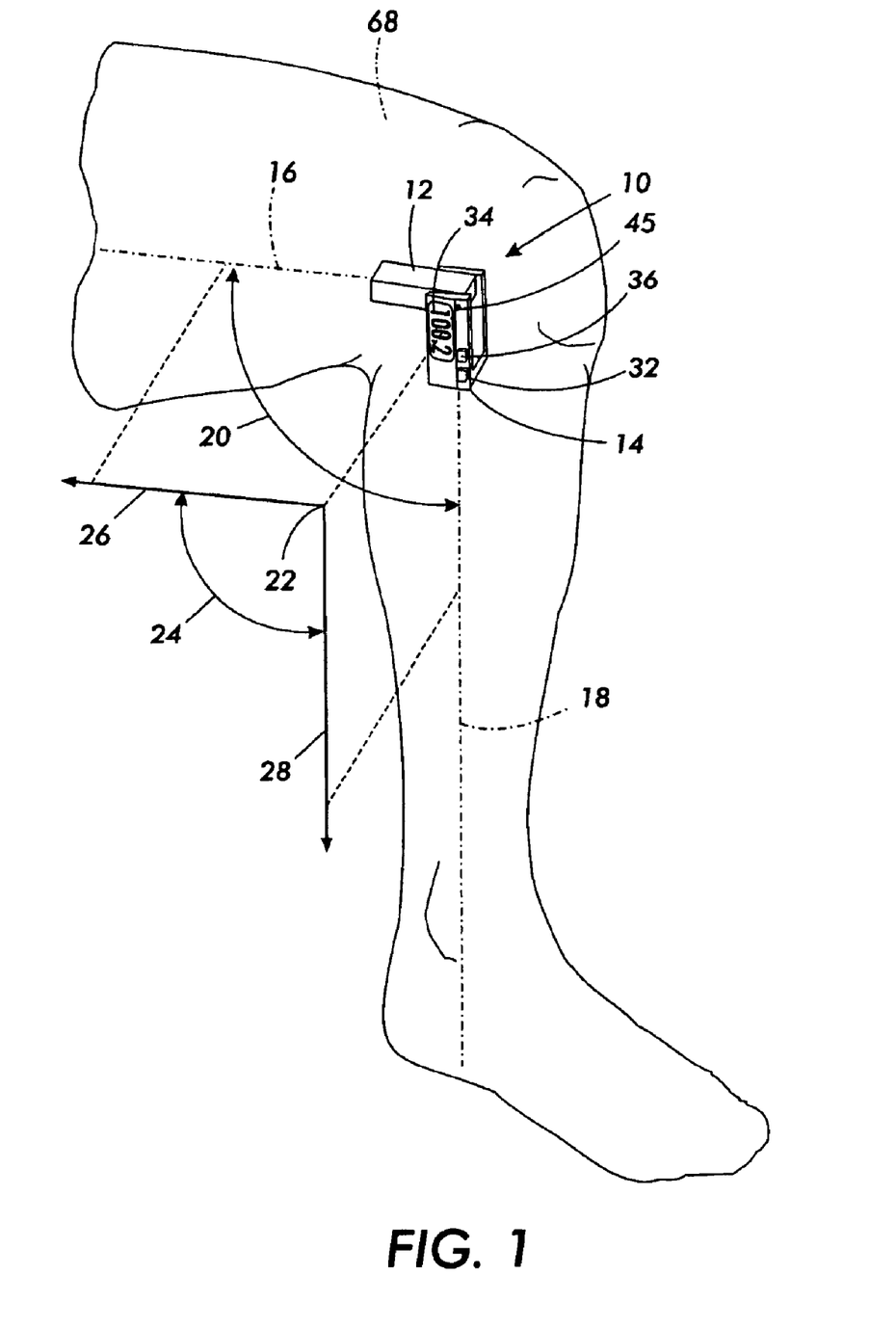
FIG. 1 is topside view of one embodiment of the light projecting goniometer, in its open position, being used to measure to angle of a joint, for example, a knee.

FIG. 1 is a schematic of device 10, one preferred embodiment of the instant invention. As is illustrated in FIG. 1, with the device of this invention one may measure any angle. To measure any angle, such as angle 24 in FIG. 1, one may place a measuring device (not shown) at vertex 22. Rays 26 and 28 then define the angle 24. In the embodiment depicted in FIG. 1, it is often difficult to define rays 26 and 28 when the objects with which they are aligned are relatively small.

Referring again to Figure, device 10 is one preferred goniometer of this invention. It will be seen that such device 10 preferably comprises means to emit light or similar radiant energy beams 16 and 18. In the embodiment depicted, these means are disposed within arms 12 and 14, respectively. Arms 12 and 14 are preferably pivotally connected to each other at pivot point 45 by means of a pivoting means 44 (not shown in FIG. 1, but see FIG. 3). The pivotal connection provided by the pivoting means 44 allows one to superimpose the light beams 16/18 over the imaginary rays 26/28 of the angle 24 to be measured.

In the preferred embodiment depicted in FIG. 1, the angle 24 to be measured corresponds to the bend of a knee joint 68, defined by angle 20.

In one embodiment, discussed elsewhere in this specification, the pivoting means 44 is connected to a means (not shown in FIG. 1) for determining the extent to which such means 44 has been pivoted. In one embodiment, the means for determining the angle maybe a linear potentiometer (not shown in FIG. 1, but see FIG. 5). In another aspect of this embodiment, the angle detected by this latter means is displayed in a display area 32.

Referring again to FIG. 1, the assembly 10 is comprised of a power switch 34 and a reset/calibrate switch 36.

Figure 2:
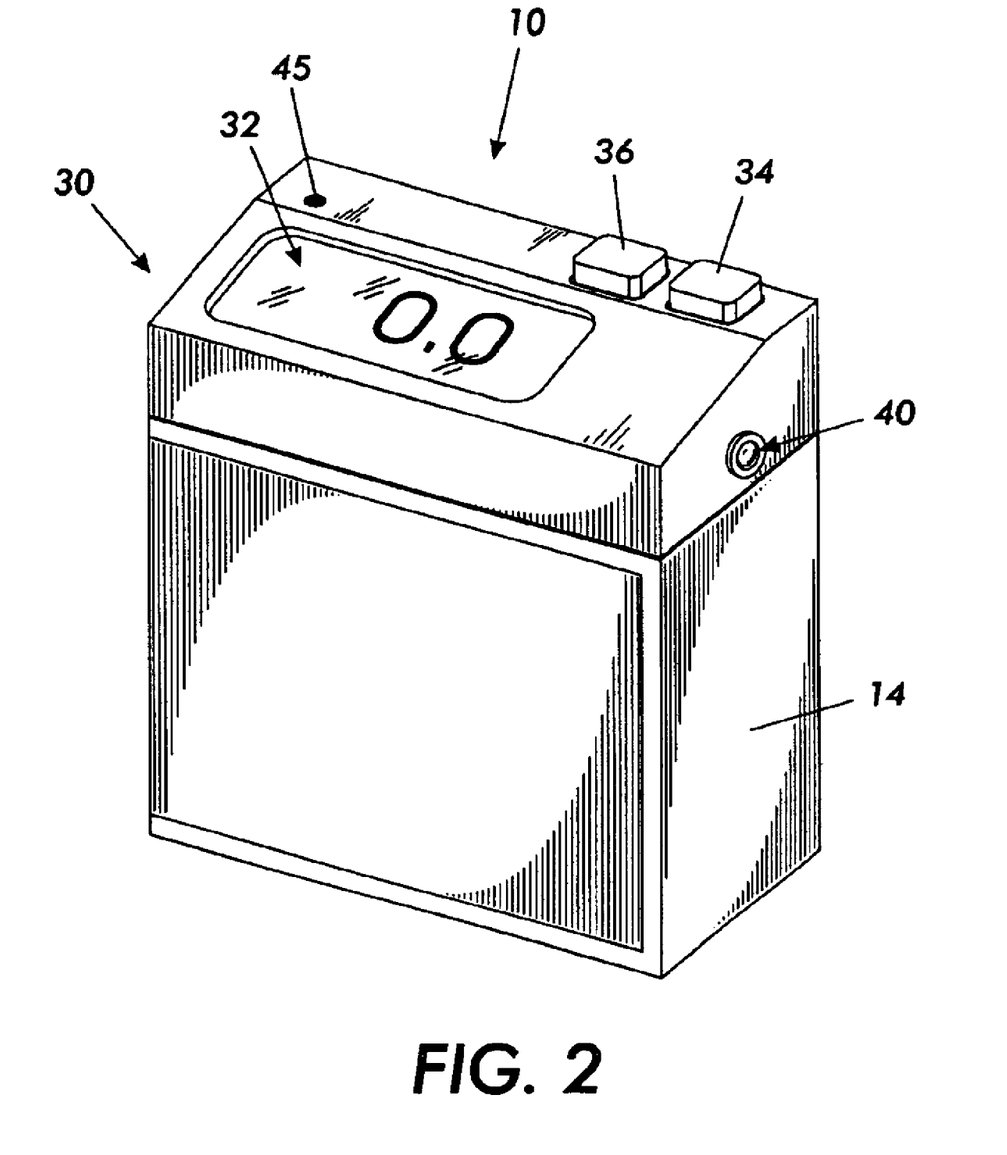
FIG. 2 is a perspective view of one embodiment of the light projecting goniometer in its closed position.

FIG. 2 is a perspective view of the device 10 of FIG. 1, shown it in its closed position. Referring to FIG. 2, it will be seen that, in the embodiment depicted, the arm 12 is of an appropriate size and configuration to fit inside of arm 14. Thus, the device may conveniently be stored in a "closed" position when not in use; in such closed position, it forms a substantially rectangular assembly. In one embodiment of the invention, the device is approximately 3 inches in height, 1.75 inches in width and 0.75 inches in thickness and weighs less than 0.5 kilogram. In another embodiment, the device is approximately 1 inch in height, 0.5 inches in width, and 0.25 inches in thickness and weighs less than 0.25 kilograms. In another embodiment the device is less than 1 cm in height, less than 0.5 inches in width, less than 0.25 inches in thickness, and weighs less than 50 grams.

Referring again to FIG. 2, and in the preferred embodiment depicted therein, a control panel 30 is mounted on arm 14. In the embodiment depicted, the control panel 30 is mounted atop arm 14. In another embodiment, not shown, the control panel 30 is mounted on the side of arm 14. Additionally, the control panel may comprise means to control the intensity of the light beams, means to indicate a low battery, and means to relay the measured angle to a data storage device.

Referring again to FIG. 2, it will be seen that disposed on and within control panel 30 are a plurality of device controls and displays, including, for example, reset switch 36, power switch 34, and display 32. Visible on the side of the device is light emission point 40. In one embodiment reset switch 36 is used to "zero" the device such that display 32 reads an angle of zero degrees. In another embodiment, power switch 34 is used to turn the light sources off so as to prolong the lifetime of the power source.

Figure 3:
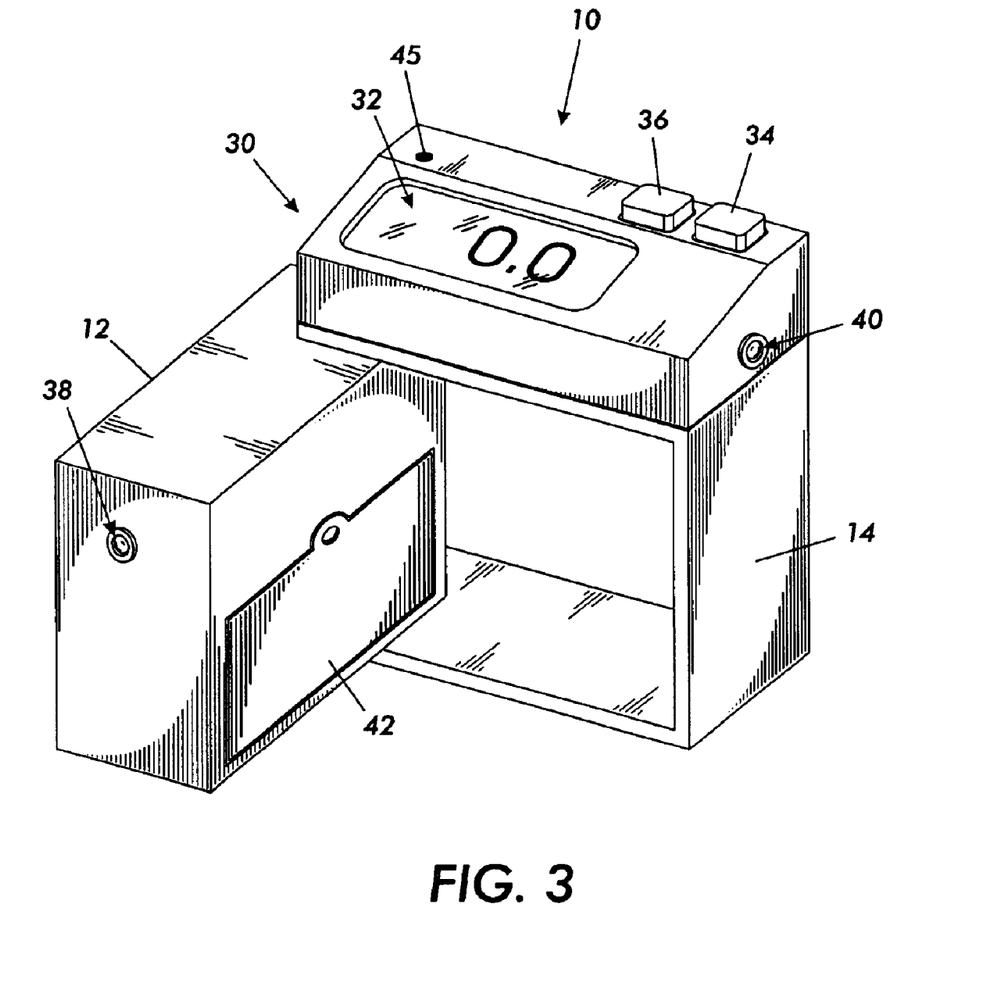
FIG. 3 is a perspective view of one embodiment of the light projecting goniometer in its open position.

FIG. 3 is a schematic illustration of the device 10. FIG. 3 depicts the device 10 in one of its "open" positions. Control panel 30 is visible in this configuration. In this embodiment, disposed within control panel 30 are power switch 34, reset switch 36, and display 32.

The display 32 may be any device for displaying the measured angle, such as a liquid crystal display, a light-emitting diode display or any of a number of display types employed in personal digital devices such as cellular phones, etc.

Referring again to FIG. 3, and in the embodiment depicted, the control panel 30 is mounted atop arm 14.

Housed within arm 14 is a light source 46 (not shown in FIG. 3, but see FIG. 4) which projects a beam of light from light emission point 40. Arm 12 is likewise equipped with a light source 47 (not shown in FIG. 3, but see FIG. 4) that preferably projects a beam of light from light emission point 38. The light emission point 40 may be a hole in the housing of the arm 14, or other means for delivering light, such as, for example, a fiber optic cable (not shown).

Referring again to FIG. 3, it will be appreciated that, housed within arm 14 is a power supply (not shown) disposed behind access panel 42, which may be, for example, a battery. The power supply is preferably adapted to deliver from about 1 to about 12 volts of direct current. It is preferred that an access panel 42 be removable so as to allow replacement of the power supply. Access panel 42 may be secured to device 42 by securing means, such as frictionally restrained by snap locks or securing by screws.

In another embodiment, not shown, a power supply may be used that is disposed external to arm 14 and to device 10 and connected to circuitry therein via a wire lead and jack as is commonly known for portable devices.

Referring again to FIG. 3, arm 12 and arm 14 are pivotally connected to one another by pivot means 44 (not shown in FIG. 3, but see FIG. 4) at pivot point 45. The pivoting means may be, for example, a hinge (not shown in FIG. 3, but see 44 in FIG. 4).

Figure 4:
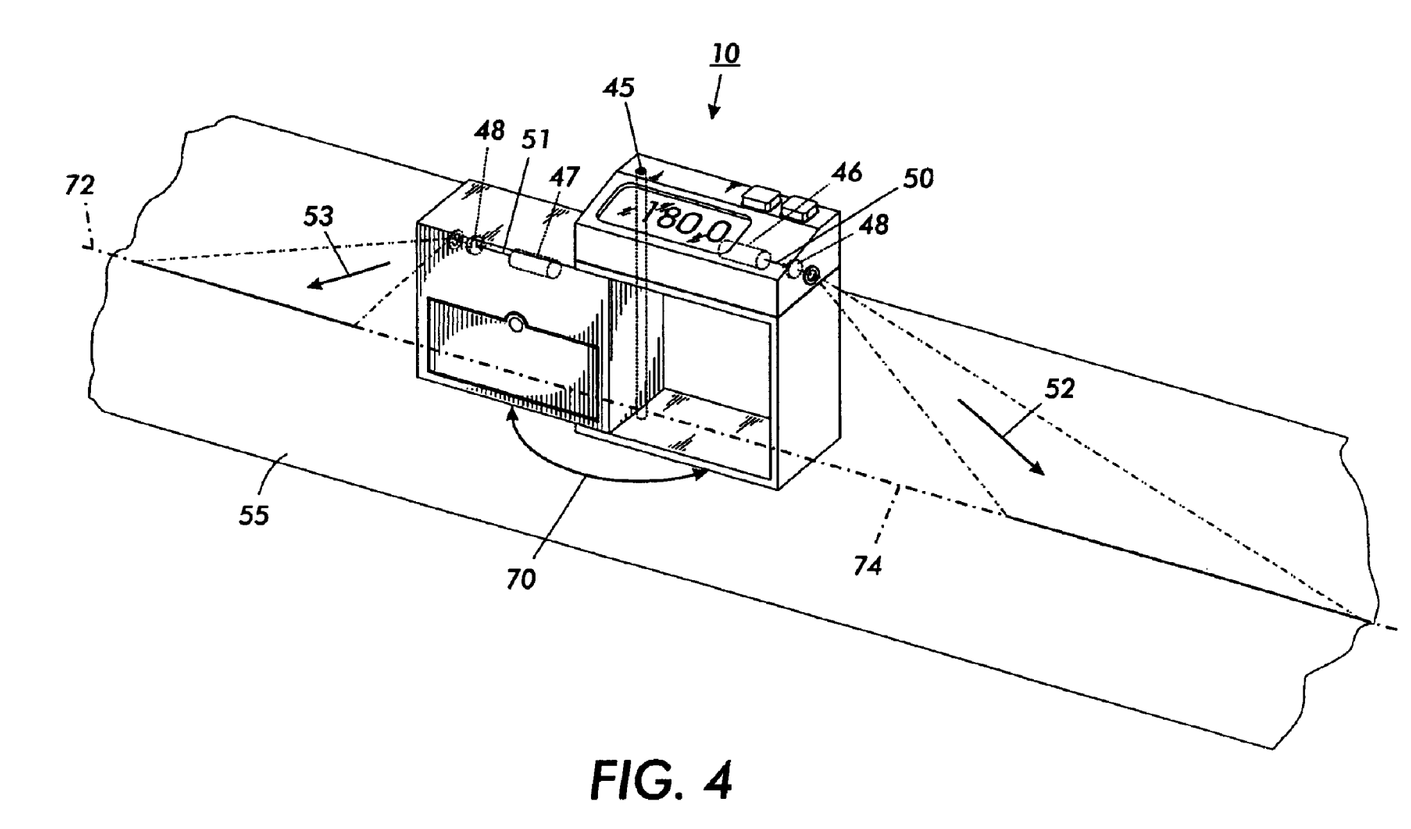
FIG. 4 is a partially transparent view of one embodiment of the light projecting goniometer showing the inner structure of one arm of the device.

FIG. 4 is a schematic view of goniometer 10. Referring to FIG. 4, and the embodiment depicted therein, it will be seen that device 10 includes of a beam splitter 48.

In the embodiment depicted in FIG. 4, the light source 46 preferably provides at least one light beam 50. In one aspect of this embodiment, the light beam 50 has a wavelength of from about 600 nanometers to about 700 nanometers.

As is known to those skilled in the art, a beam splitter is an optical device for dividing a beam into two or more separate beams. As will be apparent, the beam splitter 48 allows one to redirect a light beam so as to project light on a surface directly in front of the device. This allows the beams 52/53 to be easily visualized on the surface 55 and greatly aids in visualizing the two rays 72/74 of the angle 70 to be measured. An example of such redirection may be seen in FIG. 4.

Referring again to FIG. 4, it will be seen that, in the embodiment depicted, light source 46 emits a beam of light in the direction of arrow 50. When the beam contacts redirection means 48, the path of the light is altered such that some of the light is projected in the direction of arrow 52. Additionally, as is illustrated in FIG. 4, such redirection may also include spreading of the light 50, so that a line 52, as opposed to a single point, may be produced on the surface 55 where the beam strikes in front of the device 10.

Such beam splitters and expanders are well known within the art and may be comprised of a wide variety of materials, including, but not limited to, mirrors, plastics, glass etc. Reference may be had to U.S. Pat. Nos. 5,822,124; 4,645,302; 4,125,864.

Figure 5:
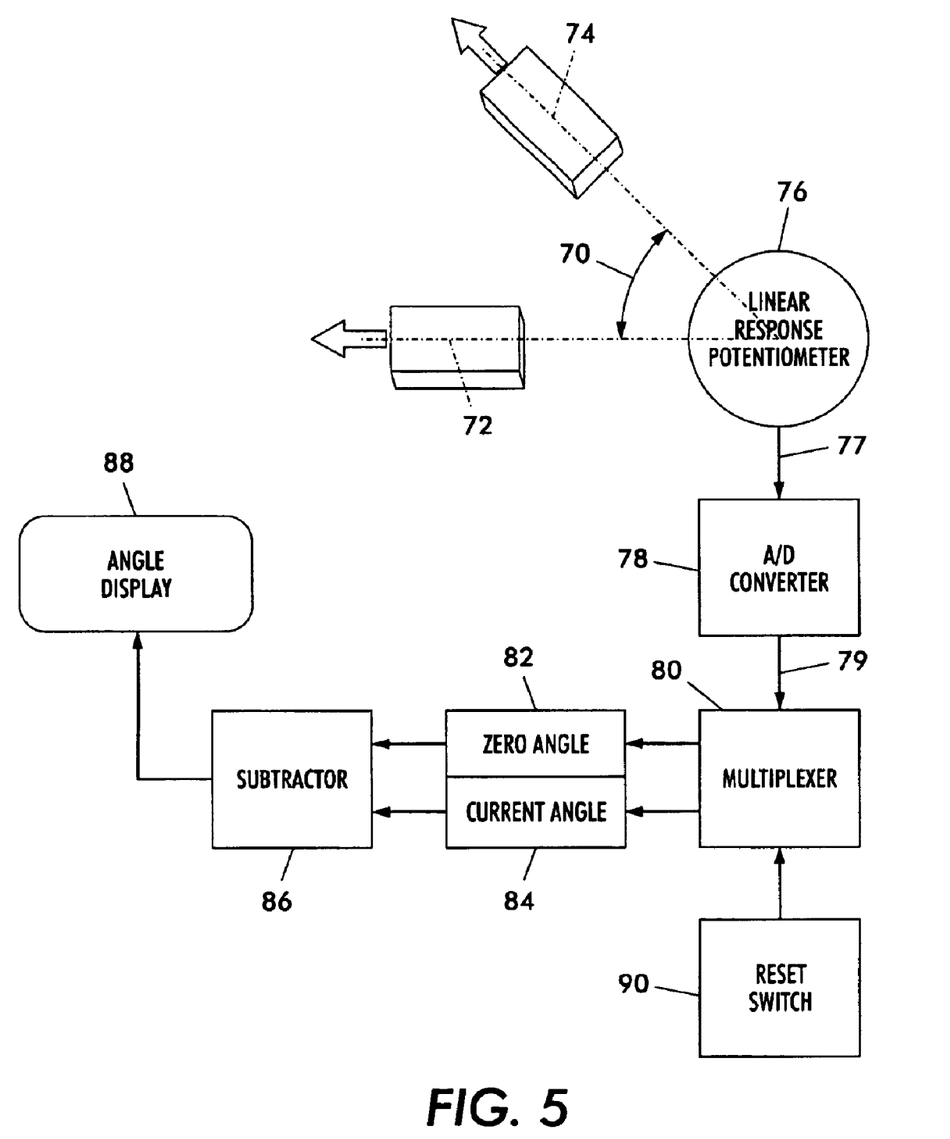
FIG. 5 is a schematic block diagram illustrating one embodiment of the invention.

FIG. 5 is a schematic block diagram of an electronic circuit for detecting the angle between the first and second light beams. As may be seen in FIG. 5, and in the embodiment depicted therein, linear response potentiometer 76 provides an analog signal 77 to an analog/digital (A/D) converter 78. Analog signal 77 is proportional to the angle 70 between rays 72 and 74. The A/D converter 78 produces digital signal 79, which is provided to multiplexer 80. Multiplexer 80 routes digital signal 79 to memory location 84 ("current angle") if reset switch 90 is not activated.

Alternately, if reset switch 90 is depressed, multiplexer 80 stores the value of signal 79 in memory location 82 ("zero angle"). Subtractor 86 then calculates the difference between the value currently in memory location 82 ("zero angle") and memory location 84 ("current angle") and continuously displays the result in angle display 88. It will be appreciated that although described as a "digital" storage and manipulation device, the present invention may be implemented using equivalent analog devices to store/zero and measure the angle between the beams. It should be further appreciated that the present invention may be adapted to include additional data storage and/or display capability in order to facilitate its use in a variety of situations by physical therapists and the like.

Figure 6:
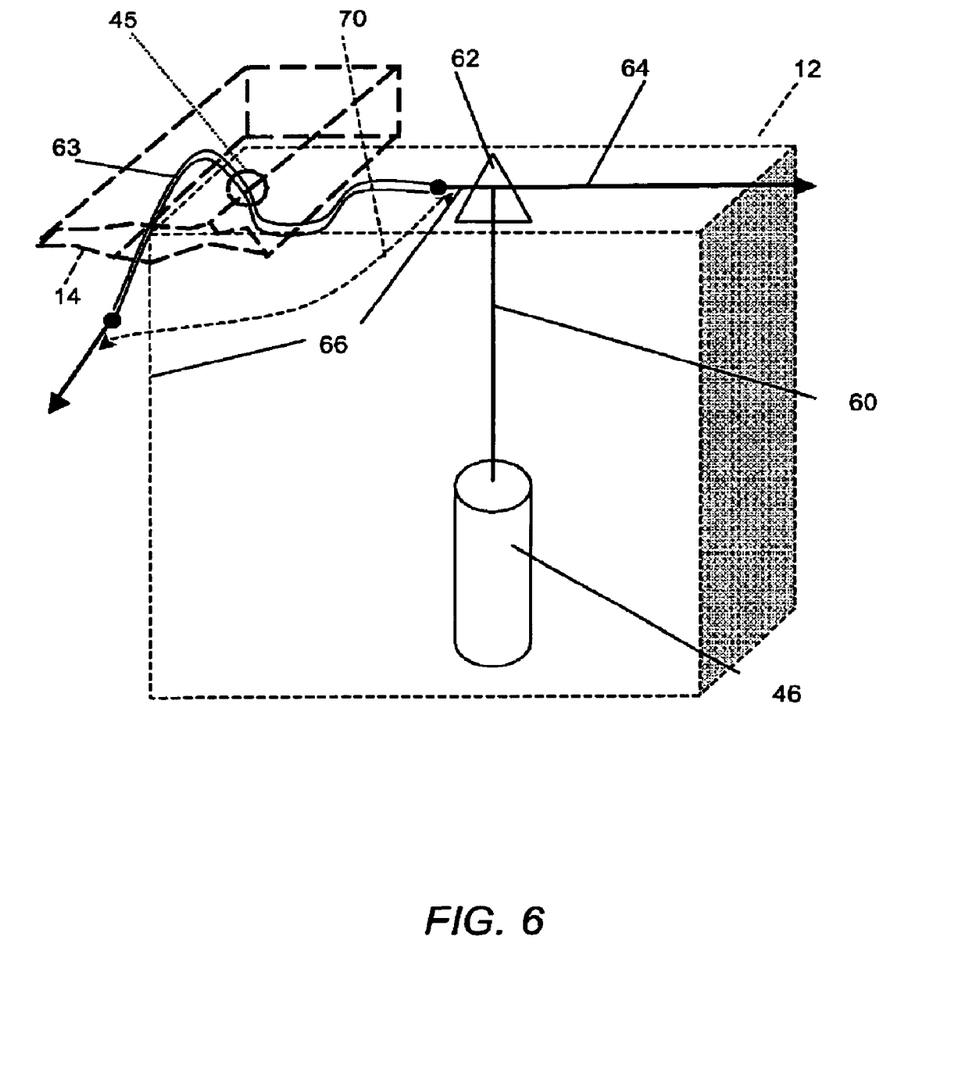
FIG. 6 is a schematic view of an alternative embodiment of the present invention.

In an alternative embodiment depicted in FIG. 6, only one light source is used. In this embodiment a single light source 46 generates a light beam 60 that is split into two or more independent beams 64 and 66. Such splitting means may include, for example, a beam splitter 62, a reflective surface, and/or fiber optic cables 63. The device is adapted to measure the angle 70 between the two light beams, irrespective of the fact that the two beams originated from the same light source.

The larger the goniometer is, the more difficult is its use for measuring small angles, such as those found on digits or fingers. It may be advantageous to minimize the size of the goniometer so as to make it useful with small joints. It should be noted that the instant goniometer is useful for a wide range of joint sizes. The small size of the device allows it to be used at small joints, such as fingers. Likewise, its long light beams, which serve the function of arms, are suitable for use at large joints such as the knee, elbow, hip, etc.

It is understood that the aforementioned description is illustrative only and that changes can be made in the apparatus, in the components and their proportions, and in the sequence of combinations and process steps, as well as in other aspects of the invention discussed herein, without departing from the scope of the invention as defined in the following claims.

I claim:

1. An apparatus for measuring an angle, comprising:
   a means for producing a first beam of light; a means for producing a second beam of light, wherein said second beam of light is pivotably adjustable so as to move relative to said first beam of light, wherein said means for producing a first beam of light and means for producing a second beam of light comprises:
   a common light source, and
   splitting means for splitting a beam output by said common light source into the first beam of light and the second beam of light;
   means for redirecting at least one of said first and second beams of light from a linear path so as to spread the light and thereby produce a line on a surface where the redirected beam strikes the surface;
   circuitry for detecting the angle between the first beam of light and the second beam of light and producing an analog signal indicative thereof; and
   a display for displaying an angular value in response to the analog signal.

2. The apparatus of claim 1, further comprising means for displaying said angle between the first beam of light and the second beam of light.

3. The apparatus of claim 2, wherein means for displaying said angle is a liquid crystal display.

4. The apparatus of claim 1, wherein said circuitry for detecting the angle between the first beam of light and the second beam of light includes:
   a. a potentiometer having a linear output over a range of rotational motion, said potentiometer having a one component operatively associated with the first beam of light and a second component operatively associated with the second beam of such that a change in the angle between the first beam of light and the second beam of light results in a change of the resistance of the potentiometer;
   b. means for measuring the resistance of the potentiometer at a first angle between the beams of light and generating a first signal;
   c. means for measuring the resistance of the potentiometer at a second angle between the beams of light and generating a second signal; and
   d. a subtractor for automatically comparing the first and second signals and producing an output indicative of the difference between the first and second signals.

5. A goniometer for measuring a range of angular motion of a joint, comprising:
   a first arm of the goniometer, said first arm emitting a first laser beam of light from an end thereof in a manner parallel to the first arm;
   a second arm pivotably connected to said first arm, said second arm emitting a second laser beam of light from an end thereof in a manner parallel to the second arm, wherein said first and second laser beams are produced by a common laser light source, and second beam splitter for splitting a laser beam output by said common light source into the first laser beam and the second laser beam;
   a first beam splitter for redirecting at least one of said first and second beams of laser light from a linear path so as to spread the light and thereby produce a line on a surface where the redirected beam strikes the surface, said surface lying generally parallel and beneath one arm of the goniometer;
   a linear potentiometer for detecting an angle between the first arm and its first beam of light and the second arm and its second beam of light and generating a signal representing the angle;
   memory for storing at least one signal representing a first angle between the first arm and the second arm; and
   a subtractor for automatically determining, based upon the potentiometer signal, the angular difference between the first angle and a current angle as the joint is moved, thereby characterizing the range of angular motion; and
   a display for displaying the angular difference.

* * * * *